(12) United States Patent
Lentrichia et al.

(10) Patent No.: US 6,939,672 B2
(45) Date of Patent: Sep. 6, 2005

(54) NUCLEIC ACID EXTRACTION SOLUTION AND USE THEREOF

(75) Inventors: Brian Lentrichia, Acton, MA (US); Menashi A. Cohenford, West Warwick, RI (US)

(73) Assignee: Cytyc Corporation, Marlborough, MA (US)

( * ) Notice: Subject to any disclaimer, the term of this patent is extended or adjusted under 35 U.S.C. 154(b) by 471 days.

(21) Appl. No.: 10/053,349

(22) Filed: Jan. 15, 2002

(65) Prior Publication Data

US 2002/0150937 A1 Oct. 17, 2002

Related U.S. Application Data

(60) Provisional application No. 60/261,845, filed on Jan. 15, 2001.

(51) Int. Cl.$^7$ .......................... C12Q 1/68; C07H 21/00
(52) U.S. Cl. ................ 435/6; 435/5; 536/23.1
(58) Field of Search ........................ 435/5, 6; 536/23.1

(56) References Cited

U.S. PATENT DOCUMENTS

| | | | |
|---|---|---|---|
| 2,748,171 A | 5/1956 | Finch et al. | |
| 5,124,444 A | 6/1992 | Van Ness et al. | |
| 5,942,391 A | 8/1999 | Zhang et al. | |
| 6,503,716 B1 * | 1/2003 | Lai et al. ...................... | 435/6 |

FOREIGN PATENT DOCUMENTS

| | | |
|---|---|---|
| WO | WO 98/14465 | 4/1998 |
| WO | WO 98/16653 | 4/1998 |
| WO | WO 00/77235 A1 | 12/2000 |
| WO | WO 02/44400 A2 | 6/2002 |

OTHER PUBLICATIONS

Lentrichia BB et al, "Detection of *Chlamydia trachomtis* and *Neisseria gonorrhea* from liquid–based Pap collection using a novel extraction method and rapid thermal cycling with real–time detection by molecular Beacons", International Journal of Std & AIDS, vol. 12, No. Supplemental 2, 2001, p. 115, XP00811932.

Gevaudant, et al,"An improved method for isolating polyphenol–fre RNA from woody plant tissue" Database Biosis online, Biosciences Information Service, Philadelphia, PA, US, Nov. 1999, Databse accession No. PREV20000005773; XP–0022275684.

* cited by examiner

*Primary Examiner*—Jezia Riley
(74) *Attorney, Agent, or Firm*—Theodore Allen; Mark J. Casey

(57) ABSTRACT

Disclosed are methods and compositions for extracting nucleic acids from a biological sample. In particular, disclosed is a nucleic acid extraction solution together with methods using such a solution for extracting nucleic acid sequences from biological samples containing cells, cellular debris or both. The nucleic acid extraction solution contains a molecule having the formula $R_1O-CH_2-CH_2-OR_2$, wherein $R_1$ and $R_2$ independently are selected from the group consisting of hydrogen and an alkyl group.

17 Claims, No Drawings

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Forward primer

<400> SEQUENCE: 1
tccggagcga gttacgaaga                                              20

<210> SEQ ID NO 2
<211> LENGTH: 20
<212> TYPE: DNA
<213> ORGANISM: Artificial Sequence
<220> FEATURE:
<223> OTHER INFORMATION: Reverse primer

<400> SEQUENCE: 2
aatcaatgcc cgggattggt                                              20

<210> SEQ ID NO 3
<211> LENGTH: 42
<212> TYPE: DNA
<213> ORGANISM: Artificial Sequence
<220> FEATURE:
<223> OTHER INFORMATION: a probe (molecular beacon) specific for
      Chlamydia trachomatis

<400> SEQUENCE: 3
ccgtcactgg gagaaagaaa tggtaggttg ttggaatgac gg                     42

<210> SEQ ID NO 4
<211> LENGTH: 20
<212> TYPE: DNA
<213> ORGANISM: Artificial Sequence
<220> FEATURE:
<223> OTHER INFORMATION: Forward primer

```
<400> SEQUENCE: 4
tcttttctct ctgacggttc                                              20

<210> SEQ ID NO 5
<211> LENGTH: 20
<212> TYPE: DNA
<213> ORGANISM: Artificial Sequence
<220> FEATURE:
<223> OTHER INFORMATION: Reverse primer

<400> SEQUENCE: 5
aggttggaga ttagtcagat                                              20

<210> SEQ ID NO 6
<211> LENGTH: 20
<212> TYPE: DNA
<213> ORGANISM: Artificial Sequence
<220> FEATURE:
<223> OTHER INFORMATION: HO1 primer

<400> SEQUENCE: 6
gctacgcata cccgcgttgc                                              20

<210> SEQ ID NO 7
<211> LENGTH: 20
<212> TYPE: DNA
<213> ORGANISM: Artificial Sequence
<220> FEATURE:
<223> OTHER INFORMATION: HO3 primer

<400> SEQUENCE: 7
cgaagacctt cgagcagaca                                              20

<210> SEQ ID NO 8
<211> LENGTH: 22
<212> TYPE: DNA
<213> ORGANISM: Artificial Sequence
<220> FEATURE:
<223> OTHER INFORMATION: Forward primer

<400> SEQUENCE: 8
gtcttcgttt ccaacaggtc ta                                           22

<210> SEQ ID NO 9
<211> LENGTH: 20
<212> TYPE: DNA
<213> ORGANISM: Artificial Sequence
<220> FEATURE:
<223> OTHER INFORMATION: Reverse primer

<400> SEQUENCE: 9
tagcgatatg gagcgtcaag                                              20

<210> SEQ ID NO 10
<211> LENGTH: 38
<212> TYPE: DNA
<213> ORGANISM: Artificial Sequence
<220> FEATURE:
<223> OTHER INFORMATION: a molecular beacon probe specific for
      Neisseria gonorrhoeae

<400> SEQUENCE: 10
tggacgctct gtttcggctc tctgctgttt caagtcca                          38
```

NUCLEIC ACID EXTRACTION SOLUTION AND USE THEREOF

RELATED APPLICATIONS

This application claims the benefit of U.S. Provisional Application Ser. No. 60/261,845, filed Jan. 15, 2001, the disclosure of which is incorporated herein by reference.

FIELD OF THE INVENTION

The present invention relates to a nucleic acid extraction solution and to uses thereof, and more particularly, the invention relates to a nucleic acid extraction solution containing an ethylene glycol-type reagent and to uses thereof.

BACKGROUND OF THE INVENTION

Nucleic acid-based assays have a wide variety of applications in the biological sciences. One important application is the detection of certain nucleic acid sequences in a biological sample. This type of assay has become useful in determining whether certain organisms, for example, microbial or viral pathogens (for example, *Chlamydia trachomatis* (CT), *Neisseria gonorrhoeae* (GC), or human papillomavirus (HPV)), are or have been present in a particular sample of interest. This can be helpful in determining whether an individual of interest, for example, a human, has or has not been infected with a particular organism. This type of information can be important for treating or managing the health of an individual.

A variety of nucleic acid extraction solutions have been developed over the years for extracting nucleic acid sequences from a sample of interest. See, for example, Sambrook et al. (Eds.) Molecular Cloning, (1989) Cold Spring Harbor Press. Many such methods typically require one or more steps of, for example, a detergent-mediated cell lysis step, a proteinase treatment step, a phenol and/or chloroform extraction step, and an alcohol precipitation step. Such methods typically require multiple steps, and can be time consuming. Inadvertent omission or improper sequence of one or more steps may result in less efficient nucleic acid extraction. Furthermore, when extracting nucleic acids from multiple samples, the more steps a particular method has, the more likely it is that samples become cross-contaminated during processing. When the resulting nucleic acid sample is analyzed, for example, by using an amplification-based protocol, for example, via polymerase chain reaction, cross-contamination may lead to false-positive results, which, in a clinical setting, may be significant.

Accordingly, it is desirable to produce a nucleic extraction solution that can be used in a simple, quick, and reliable nucleic acid extraction protocol that minimizes the risk of cross-contamination between samples, and that the resulting nucleic acids may be analyzed using conventional methodologies. These and other objects and features of the invention will be more clearly understood from the following description and claims.

SUMMARY OF THE INVENTION

The present invention provides a nucleic acid extraction solution containing an ethylene glycol-type reagent and methods using such an extraction solution. Once extracted by the solution of the invention, the isolated nucleic acid samples can be analyzed to determine whether particular nucleic acid sequences, for example, microbial or viral nucleic acid sequences, are present in a biological sample of interest. As a result, the methods and compositions can be used to determine quickly and reliably whether microbial or viral nucleic acids are present in the sample, which can thus act as an indicator of microbial or viral infection or contamination. The nucleic acid extraction solution can be used to extract nucleic acids of interest, for example, microbial or viral nucleic acids from biological samples containing cells and/or cellular debris, for example, biological samples containing mammalian cells and/or mammalian cell debris.

In one aspect, the nucleic acid extraction solution comprises an ethylene glycol-type reagent or an ethylene glycol derivative having the formula $R_1O-CH_2-CH_2-OR_2$. $R_1$ and $R_2$ are selected independently from the group consisting of hydrogen and an alkyl group. Preferably, the alkyl group of $R_1$ or $R_2$ has 1–12 carbon atoms, and more preferably, has 1–6 carbon atoms. More specifically, the alkyl group is selected from the group consisting of methyl, ethyl, n-propyl, iso-propyl, n-butyl, iso-butyl, sec-butyl, tert-butyl, n-pentyl, iso-pentyl, n-hexyl, and iso-hexyl. In a preferred embodiment, the alkyl group is selected from the group consisting of methyl, ethyl, n-butyl, iso-butyl, sec-butyl and tert-butyl.

In a preferred embodiment, $R_1$ and $R_2$ simultaneously are not both hydrogen atoms. More preferably, when $R_1$ is a methyl group, an ethyl group or a butyl group, $R_2$ is hydrogen. The ethylene glycol-type reagent preferably is 2-methoxyethanol, 2-ethoxyethanol or 2-n-butyloxyethanol. Most preferably, the reagent is 2-methoxyethanol.

In another preferred embodiment, the solution comprises from about 0.5% (v/v) to about 5% (v/v) of the reagent. More preferably, however, the solution comprises about 1% (v/v) of the reagent.

In another preferred embodiment, the solution optionally comprises a buffering agent. It is contemplated that a variety of buffering agents may be useful in the practice of the invention, however, the buffering agent preferably is a Tris buffer, a MOPS buffer or a borate buffer. In another embodiment, the solution preferably has a pH greater than about 7. The solution preferably has a pH in the range from about 7 to about 13, and under certain circumstances the solution preferably has a pH of from about 9 to about 11.

In another embodiment, the solution optionally further comprises a detergent. Although a variety of detergents can be useful in the practice of the invention, preferred detergents include, for example, Tween®, Brij®, and Triton-X100®. In addition, the solution may further comprise a chaotropic salt, for example, a guanidium salt, for example, guanidium thiocyanate.

In another aspect, the invention provides a method of extracting nucleic acids from a biological sample. The sample may be derived from a mammal, more specifically, a human, and may be, for example, a tissue sample, body fluid sample, or another cell containing sample, for example, a cervical smear. The method comprises mixing the biological sample with a nucleic acid extraction solution comprising a reagent having the formula $R_1O-CH_2-CH_2-OR_2$. $R_1$ and $R_2$ independently are selected from the group consisting of hydrogen and an alkyl group. In a preferred embodiment, the alkyl group of $R_1$ or $R_2$ has 1–12 carbon atoms, more preferably, has 1–6 carbons. The alkyl group preferably is selected from the group consisting of methyl, ethyl, n-propyl, iso-propyl, n-butyl, iso-butyl, sec-butyl, tert-butyl, n-pentyl, iso-pentyl, n-hexyl, and iso-hexyl. More preferably, the alkyl group is selected from the group consisting of methyl, ethyl, n-butyl, iso-butyl, sec-butyl and tert-butyl.

In a preferred embodiment, $R_1$ and $R_2$ simultaneously are not both hydrogen atoms. For example, when $R_1$ is methyl, ethyl, n-butyl, iso-butyl, sec-butyl or tert-butyl, $R_2$ is hydrogen. The solution preferably comprises from about 0.5% (v/v) to about 5% (v/v) of the reagent. More preferably, however, the solution comprises less than about 5% (v/v) of the reagent. Most preferably, the solution comprises about 1% (v/v) of the reagent.

In another embodiment, the solution optionally further comprises a buffering agent for maintaining the pH of the solution. Preferred buffering agents include, for example, a Tris or Tris-like buffer, a MOPS buffer or a borate buffer. Most preferably, the buffer is a borate buffer. The solution preferably has a pH greater than about 7. More preferably the solution has a pH in the range from greater than about 7 to less than about 13, and in certain circumstances, the solution has a pH in the range from about 9 to about 11. In a preferred embodiment, the solution comprises about 1% (v/v) 2-methoxyethanol and borate buffer, pH 9.5. A buffering agent, therefore, preferably has a pKa of greater than about 7.

In another embodiment, the solutions optionally further comprises a detergent. A variety of detergents may be used in the practice of the inventions, however, preferred detergents include, for example, Tween®, Brij®, and Triton®-X100. In addition, the solution optionally may further comprise a chaotropic salt, for example, a guanidium salt.

In another embodiment, the extraction method comprises an additional step of heating the mixture to a temperature within the range from about 50° C. to about 100° C., more preferably from about 75° C. to about 100° C., and most preferably from about 90° C. to about 100° C. The method, however, preferably lacks one or more of a phenol extraction step, a chloroform extraction step or an alcohol, for example, ethanol, precipitation step.

In another embodiment, the method comprises the optional, additional step of detecting, for example, via hybrid capture or other hybridization protocol, a particular nucleic acid sequence, for example, a microbial or viral nucleic acid sequence, in the sample. This method can be used to determine simultaneously the presence or absence of one or more contaminating agents, for example, microbial or viral pathogens, in the sample. Prior to detecting the nucleic acid sequence, the method of the invention may also include an optional step of amplifying the nucleic acid sequence of interest by, for example, polymerase chain reaction, ligase chain reaction, or the like.

DETAILED DESCRIPTION OF THE INVENTION

In its most general application, the present invention provides a nucleic acid extraction solution containing an ethylene glycol-type reagent and methods of using such an extraction solution. Once extracted from a biological sample, the nucleic acids can be analyzed to determine whether one or more particular nucleic acid sequences, for example, microbial and/or viral nucleic acid sequences, are present in the sample. As a result, the methods and compositions can be used to determine quickly and reliably whether there are microbial and/or viral nucleic acid sequences in the biological sample.

The nucleic acid extraction solution of the invention comprises a molecule having the formula $R_1O—CH_2—CH_2—OR_2$. $R_1$ and $R_2$ independently are selected from the group consisting of hydrogen and an alkyl group. Preferably, the alkyl group of $R_1$ or $R_2$ has 1–12 carbon atoms, and, more preferably, has 1–6 carbon atoms. More specifically, the alkyl group is selected from the group consisting of methyl, ethyl, n-propyl, iso-propyl, n-butyl, iso-butyl, sec-butyl, tert-butyl, n-pentyl, iso-pentyl, n-hexyl, and iso-hexyl.

In a preferred embodiment, $R_1$ and $R_2$ are not simultaneously both hydrogen atoms. In a preferred embodiment, the alkyl group is selected from the group consisting of methyl, ethyl, and butyl. More preferably, when $R_1$ is a methyl group, an ethyl group or a butyl group, $R_2$ is hydrogen. Accordingly, the molecule preferably is 2-methoxyethanol, 2-ethoxyethanol or 2-n-butyloxyethanol. Most preferably, the molecule is 2-methoxyethanol.

An exemplary ethylene glycol-type reagent or derivative useful in the practice of the invention can be selected from the group consisting of (i) 2-methoxyethanol (also known as methyl cellosolve or ethylene glycol monomethyl ether) having the formula $CH_3—O—CH_2—CH_2—O—H$ and referred to herein as MCS; (ii) 2-ethoxyethanol (also known as cellosolve or ethylene glycol monoethyl ether) having the formula $CH_3—CH_2—O—CH_2—CH_2—O—H$ and referred to herein as 2-EE; (iii) 2-butoxyethanol (also known as butyl cellosolve or ethylene glycol monobutyl ether) having the formula $CH_3—CH_2—CH_2—CH_2—O—CH_2—CH_2—O—H$ and referred to herein as BCS; (iv) ethylene glycol having the formula $H—O—CH_2CH_2—O—H$ and referred to herein as EG; (v) 1,2-diethoxyethane (also known as ethylene glycol diethyl ether) and having the formula $CH_3—CH_2—O—CH_2—CH_2—O—CH_2—CH_3$ and referred to herein as EGDE or EGDeE, and (vi) 1,2-dimethoxyethane (also known as ethylene glycol dimethyl ether) having the formula $CH_3—O—CH_2—CH_2—O—CH_3$ and referred to herein as EGDmE.

It is contemplated that the requisite amount of ethylene glycol-type reagent useful in a nucleic extraction solution of the invention can be determined by routine experimentation. For example, nucleic acid extraction solutions containing different amounts of the reagent can be prepared and tested for their relative ability to extract nucleic acids from a biological sample of interest. The concentration of the ethylene glycol-type molecule in the extraction solution of the invention preferably is from about 0.5% (v/v) to about 5% (v/v) of the solution. A preferred concentration is about 1% (v/v). For example, with 2-methoxyethanol, the preferred concentration of 2-methoxyethanol in the extraction solution is about 1% (v/v).

In another preferred embodiment, the solution optionally comprises a buffering agent. It is contemplated that a variety of buffering agents may be useful in the practice of the invention. The choice of appropriate buffering agent, buffer concentration, and pH for a particular extraction solution may be determined by routine experimentation. Exemplary buffering agents include Tris-ammonium buffers, borate buffers and MOPS buffers. Borate buffers, however, are preferred. The pH of the extraction solution preferably is greater than about 7. The extraction solution preferably has a pH in the range from about 7 to about 13, and under certain circumstances the solution preferably has a pH of about 9 to about 11. Buffering agents preferably have a pKa greater than about 7.

Furthermore, the extraction solution may optionally comprise a detergent. It is contemplated that a variety of different detergents and detergent concentrations may be useful in the practice of the invention. However, it appears that detergents have most benefit when the pH of the extraction solution is below about 7. In addition, the extraction solution optionally may further comprise a chaotropic salt, for example, a guanidium salt. A preferred guanidium salt includes guanidium thiocyanate. In addition, the extraction solution optionally may comprise salts, for example, divalent cations, for example, $Mg^{2+}$ in the form of $MgCl_2$.

The extraction solutions of the invention permit a rapid, and reliable extraction of nucleic acids from a biological sample of interest. The biological sample may comprise cells, cellular debris, or both cells and cellular debris of eukaryotic, prokaryotic or viral origin. The extraction solutions of the invention are particularly useful in extracting nucleic acid of prokaryotic or viral origin from biological samples also containing eukaryotic cells or cellular debris (for example, nuclei, mitochondria, or some other subcellular organelle). For example, the extraction solution can be used to extract prokaryotic or viral nucleic acids from samples harvested from mammalian, more preferably, human, sources.

The biological samples may include, for example, a tissue sample (for example, a biopsy sample), a body fluid sample (for example, blood, serum, plasma, lymph, semen, vaginal secretion, breast exudate, sputum, or ascitic fluid), or another cell containing sample, for example, a cervical smear or breast lavage. The biological samples may be processed immediately or preserved in a preservative solution for subsequent processing. The methods and compositions of the invention are particularly useful in extracting nucleic acids from a cervical cell containing sample, for example, a cervical sample harvested by cervical smear and preserved in a preservative solution or a breast cell containing sample harvested by breast lavage and preserved in a preservative solution.

In the practice of the invention, the biological sample is combined and mixed with the extraction solution. Thereafter, the resulting mixture preferably is heated, for example, to a temperature greater than about 50° C., more preferably greater than about 75° C., more preferably greater than about 90° C., and most preferably about 98° C. The heating step can be for a particular time, for example, in the range of 1 minute to 30 minutes, however, preferred heating step is for between about 5 minutes to about 15 minutes. The optimal length of the heating step can be determined by routine experimentation. Thereafter, the sample is allowed to cool and a sample of the resulting solution can be analyzed using a variety of analytical assays for nucleic acids.

The nucleic acids, once extracted from the sample, can be analyzed using a variety of molecular techniques. For example, the nucleic acid of interest may be fractionated by gel electrophoresis and visualized via UV light after ethidium bromide staining. Alternatively, the presence of a target nucleic acid may be detected via nucleic acid-based hybridization techniques, for example, by Southern blotting, Northern blotting, slot blots, dot blots or the like, using labeled probes. The probes may be labeled with one or more detectable moieties, for example, radiolabels, fluorescent labels, enzyme labels, spin labels, and the like. It is also contemplated that a target nucleic acid optionally may be amplified, for example, by polymerase chain reaction (PCR) or ligase chain reaction (LCR), prior to or concurrent with the foregoing methods.

When the extracted nucleic acid will be subjected to amplification, it is contemplated that amplification efficiency may be enhanced by the removal of PCR inhibitors. PCR inhibitors may be removed from the sample by the addition of solid particles, including, for example, silica glass beads, Chelex resin, and ion exchange resin. Accordingly, under certain circumstances, it may be helpful to add such solid particles to the nucleic acid extraction solution of the invention prior to use.

In a preferred embodiment, the presence of target nucleic acids is determined using a technique whereby the target nucleic acid is amplified via PCR and detected via real time detection. Thermal cycling machines useful for this purpose can be obtained under the trade name ROCHE LIGHTCY-CLER. It is contemplated that the choice of appropriate amplification primers and amplification conditions may be determined by routine experimentation. Real time detection can be achieved using appropriately labeled molecular beacons.

Molecular beacons are single-stranded nucleic acid probes that possess a stem-and-loop structure in which the loop portion of the molecule is a probe sequence complementary to the target nucleic acid sequence. The stem is generated by the annealing of two complementary arm sequences, each located at either end of the probe sequence. The arm sequences are unrelated (i.e., not homologous) to the target sequence and each arm is labeled at its end. A fluorescent moiety is attached to one end of the probe, for example, at the 5' end, and a fluorescence quencher is attached to the other end, for example, at the 3' end. In its nascent state, the molecular beacon emits no fluorescence because the fluorescent moiety and quencher pair are selected such that energy gained by the fluorophore is transferred to the quencher and is dissipated as heat, an occurrence that is referred to as fluorescence resonance energy transfer (FRET). Molecular beacons are described, for example, in U.S. Pat. No. 5,925,517.

At temperatures slightly above the melting temperature ($T_m$), the stem portion of a molecular beacon unfolds and exposes the probe section of the molecule to target strands. Once exposed, the beacon and target can hybridize to one another. Upon hybridization, the molecular beacon undergoes a conformational change whereby the arm sequences of the beacon are forced apart such that the fluorophore and the quencher become spatially separated from each other relative to their spatial positions in the unhybridized state. When the fluorophore is no longer in the proximity of the quenching molecule, FRET is no longer possible, and the fluorophore then emits detectable light of appropriate wavelength when excited. The type of molecular beacon can be optimized for a particular application.

Practice of the invention will be still more fully understood from the following examples, which are presented herein for illustration only and should not be construed as limiting the invention in any way.

EXAMPLE 1

Comparison of Different Ethylene Glycol-Based Extraction Solutions

A variety of extraction solutions containing different ethylene glycol-type reagents were tested for their ability to extract microbial nucleic acid sequences from cervical cell samples. The four solutions tested included: 2 mM sodium borate buffer pH 9.5 containing 1.0% (v/v) 2-methoxyethanol (Solution 1), 2 mM sodium borate buffer pH 9.5 containing 1.0% (v/v) 2-butoxyethanol (Solution 2), 2 mM sodium borate buffer pH 9.5 containing 1.0% (v/v) 2-methoxyethanol and 0.13 M guanidium thiocyanate (Solution 3), and 2 mM sodium borate buffer pH 9.5 containing 1.0% (v/v) 2-butoxyethanol and 0.13 M guanidium thiocyanate (Solution 4).

The solutions were tested for their ability to extract nucleic acid from exfoliated cervical cells collected and stored in a methanol-based cell preservative solution known as PRESERVCYT®, available from Cytyc Corporation (Boxborough, Mass.). The cell containing sample was divided into two equal portions. *Chlamydia trachomatis* elementary bodies (25,000/mL) were added to one portion and provided a positive control. The other portion without the added *Chlamydia* elementary bodies was used as a negative control. These samples then were extracted using one of the extraction solutions (Solution 1–4) via the following method.

1.0 mL of each cell containing suspension (either positive or negative control) was centrifuged for 15 minutes at 13,000 rpm to collect the cells. The supernatant was discarded and 0.2 mL of Solution 1, Solution 2, Solution 3, or Solution 4 was added to each cell pellet. The cells then were resuspended in each solution via vortex mixing, and then each sample was heated to 98° C. for 10 minutes in a hot water bath. Thereafter, the tubes were allowed to cool and then were centrifuged briefly to collect the condensate. Samples also were extracted with a control solution containing 1% Tween®-20.

The isolated nucleic acid-containing samples then were analyzed by PCR via the following method. Typical thermocycle conditions for the PCR included an initial denaturation step of 4 minutes at 95° C. followed by 35 cycles of 30 seconds of denaturation at 95° C., 30 seconds of annealing at 55° C. and 1 minute extension at 72° C. A typical DNA master mix in 25 μL aliquots contained 10 mM Tris-HCl pH 8.3, 50 mM KCL, 5 mM MgCl$_2$, 200 μM of each dNTP, 2M betaine, 50 picomoles of each primer, 2.5 units of platinum Taq polymerase (PE Biosystems Inc.) and 5 μL of each sample extract. The amplification primers used included (forward primer, SEQ ID NO: 1) 5'-TCC-GGA-GCG-AGT-TAC-GAA-GA-3' and (reverse primer, SEQ ID NO: 2) 5'-AAT-CAA-TGC-CCG-GGA-TTG-GT-3'. The resulting amplicon for *Chlamydia* was 242 bases in length. The resulting products were fractionated by gel electrophoresis on a 0.8% agarose gel, stained with ethidium bromide and visualized with UV light.

The resulting gel showed that Solutions 1–4 extracted microbial nucleic acid from the positive control samples (spiked with *Chlamydia* elementary bodies) as evidenced by the presence of a 242 base pair amplification product for each extracted sample. A similar amplification product was produced in the positive control sample extracted with 1% Tween®-20. In contrast, no amplification product was visualized in the samples of negative controls (not spiked with *Chlamydia* elementary bodies) extracted with Solutions 1 and 2.

EXAMPLE 2

Extraction Using MCS Containing Extraction Solution

Three clinical cervical cell-containing samples in PRE-SERVCYT® solution, a positive control and a negative control were extracted with either Solution 1 from Example 1, water, or via Abbott Laboratories Urine Specimen Preparation Kit (Cat No. 3B21-24). The three clinical samples were shown previously via independent methodologies to contain *Chlamydia trachomatis*. The controls were prepared as follows. Exfoliated cervical cells in PRESERVCYT® solution were separated into two portions. One portion was spiked with 12,5000 *Chlamydia trachomatis* elementary bodies/mL (positive control), and the other portion was not spiked with the elementary bodies (negative control).

The samples were extracted as described in Example 1. The samples, however, were PCR amplified with real time detection using rapid thermal cycling (LIGHTCYCLER PCR System from Roche Molecular Biochemicals, Indianapolis, Ind.) and a probe (molecular beacon) specific for *Chlamydia trachomatis*. The molecular beacon probe was 42 bases in length and had the following sequence: (5'-CCGTCACTGGGAGAAAGAAATGGTAGGTTGTTGGA ATGACGG-3') (SEQ ID NO: 3). The PCR amplification primers included a forward primer (5'-TCTTTTCTCTCTGACGGTTC-3') (SEQ ID NO: 4), and a reverse primer (5'-AGGTTGGAGATTAGTCAGAT-3') (SEQ ID NO: 5).

The 42 base molecular beacon was purchased from Midland Certified Reagent Company (Midland Tex.) and contained a FAM fluorescent probe at the 5' end and a DABCYL quencher at the 3' end. The 42 base sequence was designed with flanking regions that spontaneously form a stem-loop structure, and with a 28 nucleotide internal sequence complementary to a region of the *Chlamydia trachomatis* nucleotide sequence product (amplicon) amplified by the forward and reverse amplification primers. The molecular beacon fluoresced upon binding or hybridizing to the target amplicon sequence. Arbitrary fluorescence levels following 40 cycle of amplification are set forth in Table 1 below.

TABLE 1

| Method | Pos. Control | Neg. Control | Sample 1 | Sample 2 | Sample 3 |
|---|---|---|---|---|---|
| Water | 7.43 | 0.10 | 2.12 | 0.11 | 0.13 |
| Abbott | 12.28 | 0.06 | 10.39 | 0.88 | 1.55 |
| Solution 1 | 12.02 | 0.12 | 11.69 | 5.11 | 7.22 |

The results indicate that Solution 1 is capable of extracting microbial nucleic acid from a cervical cell containing sample, and that the resulting nucleic acid is amplifiable via PCR.

EXAMPLE 3

Extraction Solutions with Different Ethylene Glycol-Type Reagents in Combination with Different Buffers A variety of extraction solutions containing certain ethylene glycol-type reagents and buffer combinations were tested for extraction efficiency. The reagents tested included a combination of (i) 2-methoxyethanol (MCS), 2-butoxyethanol (BCS), 2-ethoxyethanol (2-EE) ethylene glycol (EG) or 1,2-diethoxyethene (EGDE) and (ii) a citrate buffer, Tris buffer or borate buffer.

Each solution was prepared and tested for its ability to extract nucleic acid that could be amplified using conventional PCR. The test solutions were used to extract cell suspension in PRESERVCYT® solution known to contain *Chlamydia trachomatis* (positive control) or known not to contain *Chlamydia trachomatis* (negative control). The positive and negative controls were extracted as follows. 500 μL of the positive or negative control was transferred to a 2 mL screw capped centrifuge tube. The samples were centrifuged at 13,000 rpm for 15 minutes to pellet the cells. The supernatant was discarded and the cells were resuspended in 200 μL of the each extraction solution being tested via vortex mixing. The resulting cell suspension was heated in a 98° C. water bath for 10 minutes. After cooling, the tubes were centrifuged to collect the condensate and the resulting cell extract stored at 4° C. (short-term storage of about 1 week) or −20° C. (long term storage) until subsequent analysis.

The samples were amplified via PCR with real time detection. The PCR amplification was performed in a 20 μL reaction mixture containing (i) 16 μL of reagent comprising 1 μM forward primer (5'-TCTTTTCTCTCTGACGGTTC-3') (SEQ ID NO: 4), 1 μM reverse primer (5'-AGGTTGGAGATTAGTCAGAT-3') (SEQ ID NO: 5), 50 nM of a molecular beacon (5'-CCGTCACTGGG-AGAAAGAAATGGTAGGTTGTTGGAATGACGG-3') (SEQ ID NO: 3), 200 μM of each dNTP, 1 unit platinum Taq (PE Biosystems, Inc.), 8.33 mM magnesium, 1× enzyme manufacturer's buffer, 0.75 M betaine, and (ii) 4 μL of each cell extract.

The samples were amplified as follows: (1) a single initiation cycle of 95° C. for 1 minute, then (2) 55 cycles each having a denaturation step (95° C. for 5 seconds with ramp of 20° C./second), a first annealing step (48° C. for 20 seconds with ramp of 5° C./second), a second annealing step (53° C. for 2 seconds with ramp of 5° C./second) and an elongation step (72° C. for 10 seconds with a ramp of 5° C./second), and then finally (3) a single cooling step (40° C. for 30 seconds with a ramp of 20° C./second). Fluorescence resulting from DNA amplicon was measured during each first annealing step and the results expressed as the threshold cycle (i.e., the cycle number when fluorescence was detected) and the absolute fluorescence (i.e., the maximal level of fluorescence achieved upon saturation). The results from the positive controls are summarized below in Table 2.

Furthermore, the data suggest that, on the whole, solutions having alkaline pHs exhibit the best performance characteristics.

TABLE 2

| Buffer | 1% MCS | | 1% BCS | | 1% 2-EE | | 1% EGDE | |
|---|---|---|---|---|---|---|---|---|
| | Threshold Cycle | Abs. Fluor. | Threshold Cycle | Abs. Fluor. | Threshold Cycle | Abs. Fluor. | Threshold Cycle | Abs. Fluor. |
| 2 mM Citrate pH 4 | n/a | 0.12 | n/a | 0.13 | n/a | 0.17 | 32.7 | 2.85 |
| 2 mM Citrate pH 5 | n/a | 0.11 | n/a | 0.03 | 49.3 | 0.35 | 32 | 3.5 |
| 2 mM Citrate pH 6 | 32.43 | 2.76 | 32.66 | 4.27 | 29 | 6.59 | 27.82 | 12.24 |
| Water | n/a | 0.08 | n/a | 0.02 | n/a | 0.11 | 29.86 | 4.84 |
| 2 mM Tris pH 8 | 36.7 | 1.52 | 33.39 | 1.82 | 30 | 2.1 | 31.45 | 2.49 |
| 2 mM Tris pH 9 | 28.13 | 8.46 | 29.37 | 10.73 | 27.3 | 10 | 27.45 | 12.69 |
| 2 mM Borate pH 9.5 | 26.73 | 13.61 | 28.43 | 12.54 | 26.2 | 13 | 26.58 | 14.81 |
| 2 mM Borate pH 10 | 27.05 | 12.14 | 27.78 | 14.08 | 25.6 | 15.1 | 25.72 | 15.77 |
| 2 mM Borate pH 11 | 26.36 | 14.76 | 27.46 | 14.64 | 25.6 | 14.84 | 26.16 | 13.99 |

The results in Table 2 indicate that all the extraction solutions were able to extract amplifiable microbial nucleic acids. The results also indicate that, in general, extraction solutions having an alkaline pH have better performance characteristics.

EXAMPLE 4

Effect of Different Detergents

In order to test whether certain detergents may enhance the performance of extraction solutions containing MCS, a variety of detergents were added to different buffered MCS containing solutions. The concentration of MCS used in each solution was maintained at 1% (v/v). The different buffers included citrate, Tris and borate. The detergents tested included Tween® 20, Brij® 35, and Triton® X-100, all of which were obtained from Sigma Chemical Company.

The samples were extracted and PCR amplified with real-time detection as described in Example 3. The results are summarized in Table 3.

EXAMPLE 5

Effect of Different Buffers

In order to test whether different buffers enhance the performance of extraction solutions containing MCS, a variety of different buffer systems were added to different MCS containing solutions. The concentration of MCS used in each solution was maintained at 1% (v/v). The different buffers tested included citrate-glycine buffer, a MOPS buffer, a Tris-Ammonium buffer and a borate buffer.

The buffers were prepared as follows. The citrate-glycine buffer was prepared as a 250 mM stock solution with citrate acid mono-hydrate (from Fisher Scientific) and glycine (from Amresco). The MOPS buffer was prepared as a 250 mM solution with MOPS (from Sigma Chemical Co.). The Tris-ammonium buffer was prepared as a 250 mM stock solution with Tris base (from Sigma Chemical Co.) and ammonium chloride (from Sigma Chemical Company). The positive and negative controls were extracted as Described in Example 3, except that the samples were heated for 5, 10

TABLE 3

| Buffer | Tween ®-20 | | Brij ®-35 | | Triton ®-X100 | | No Detergent | |
|---|---|---|---|---|---|---|---|---|
| | Threshold Cycle | Abs. Fluor. | Threshold Cycle | Abs. Fluor. | Threshold Cycle | Abs. Fluor. | Threshold Cycle | Abs. Fluor. |
| 2 mM Citrate pH 4 | n/a | 0.03 | n/a | 0.2 | n/a | 0.01 | n/a | 0.03 |
| 2 mM Citrate pH 5 | n/a | 0.05 | 38.99 | 1.51 | n/a | 0.05 | n/a | 0.11 |
| 2 mM Citrate pH 6 | 29.62 | 8.9 | n/a | 0.13 | 31.93 | 3.6 | 39.81 | 1.53 |
| water | 52.75 | 0.58 | n/a | 0.32 | n/a | 0.28 | n/a | 0.5 |
| 2 mM Tris pH 8 | 38.92 | 1.19 | n/a | 0.27 | n/a | 0.45 | 32.46 | 2.5 |
| 2 mM Tris pH 9 | 28.14 | 10.35 | 52.03 | 0.82 | 28.06 | 5.07 | 27.89 | 9.76 |
| 2 mM Borate pH 9.5 | 28.18 | 10.49 | n/a | 0.09 | 26.94 | 9.76 | 26.17 | 12.39 |
| 2 mM Borate pH 10 | 26.28 | 15.3 | 25.9 | 11 | 51.14 | 0.64 | 26.15 | 14.07 |
| 2 mM Borate pH 11 | 27.26 | 16.65 | 27.92 | 12.59 | 27.87 | 14.64 | 27.44 | 16.97 |

The results indicate that detergents may improve the extraction characteristics of certain solutions having an acidic pH. In contrast, the detergents may provide little benefit when the solutions have an alkaline pH.

or 15 minutes. The resulting extracts were PCR amplified with real time detection as described in Example 3. The results of positive samples are set forth in Tables 4, 5, 6, and 7.

TABLE 4

1% 2-Methoxyethanol and Citrate-Glycine Buffer

| Molarity (mM) of citrate glycine buffer | pH | Incubator Time (mins) | Threshold Cycle | Abs. Fluor. |
|---|---|---|---|---|
| 10 | 2.5 | 5 | 33.42 | 0.92 |
| 10 | 2.5 | 15 | | 0.91 |
| 10 | 2.5 | 15 | 41.08 | 0.5 |
| 10 | 4.5 | 5 | | 0.15 |
| 10 | 6.5 | 10 | 27.83 | 12.73 |
| 55 | 2.5 | 5 | | −0.06 |
| 55 | 2.5 | 10 | | −0.02 |
| 55 | 4.5 | 15 | | 1.13 |
| 55 | 6.5 | 5 | 10.08 | 9.06 |
| 55 | 6.5 | 5 | 5.39 | 7.79 |
| 55 | 6.5 | 15 | | 10.58 |
| 100 | 2.5 | 5 | | 0.005 |
| 100 | 2.5 | 5 | | −0.01 |
| 100 | 2.5 | 15 | | 0.02 |
| 100 | 2.5 | 15 | | 0.05 |
| 100 | 4.5 | 5 | | 0.01 |
| 100 | 4.5 | 10 | | 0.06 |
| 100 | 6.5 | 10 | 6.02 | 5.87 |
| 100 | 6.5 | 15 | 33.76 | 2.04 |
| 100 | 6.5 | 15 | 5.54 | 6.21 |

TABLE 5

1% 2-Methoxyethanol and MOPS Buffer

| Molarity (mM) of citrate glycine buffer | pH | Incubator Time (mins) | Threshold Cycle | Abs. Fluor. |
|---|---|---|---|---|
| 10 | 6.5 | 5 | 36.7 | 1.25 |
| 10 | 6.5 | 15 | 31.85 | 2.91 |
| 10 | 6.5 | 15 | 32.75 | 2.62 |
| 10 | 7 | 5 | 28.13 | 16.27 |
| 10 | 7.5 | 10 | 26.34 | 22.49 |
| 55 | 6.5 | 5 | 29.42 | 10.45 |
| 55 | 6.5 | 10 | 28.9 | 15.44 |
| 55 | 7 | 15 | 25.9 | 22.56 |
| 55 | 7.5 | 5 | 26.42 | 22.92 |
| 55 | 7.5 | 5 | 26.11 | 24.92 |
| 55 | 7.5 | 15 | 25.74 | 23.92 |
| 100 | 6.5 | 5 | | 1.03 |
| 100 | 6.5 | 5 | 25.67 | 19.09 |
| 100 | 6.5 | 15 | 29.43 | 10.43 |
| 100 | 6.5 | 15 | 33.94 | 2.1 |
| 100 | 7 | 5 | 25.85 | 20.92 |
| 100 | 7 | 10 | 25.71 | 23.29 |
| 100 | 7.5 | 10 | 25.93 | 24.48 |
| 100 | 7.5 | 15 | 25.61 | 27.68 |
| 100 | 7.5 | 15 | 25.62 | 26.29 |

TABLE 6

1% 2-Methoxyethanol and Tris-ammonium Buffer

| Molarity (mM) of citrate glycine buffer | pH | Incubator Time (mins) | Threshold Cycle | Abs. Fluor. |
|---|---|---|---|---|
| 10 | 7.5 | 5 | 26.37 | 29.42 |
| 10 | 7.5 | 15 | 28.25 | 25.45 |
| 10 | 7.5 | 15 | 28.82 | 22.05 |
| 10 | 8.5 | 5 | 28.66 | 10.43 |
| 10 | 9.5 | 10 | 25.56 | 30.91 |
| 55 | 7.5 | 5 | 27.23 | 24.72 |
| 55 | 7.5 | 10 | 27.55 | 25.9 |
| 55 | 8.5 | 15 | 25.82 | 31.12 |
| 55 | 9.5 | 5 | 25.73 | 32.65 |
| 55 | 9.5 | 5 | 25.95 | 34.13 |
| 55 | 9.5 | 15 | 25.58 | 31.66 |
| 100 | 7.5 | 5 | 26.97 | 26.13 |
| 100 | 7.5 | 5 | 27.05 | 26.24 |
| 100 | 7.5 | 15 | 26.81 | 27.47 |
| 100 | 7.5 | 15 | 27.35 | 19.01 |
| 100 | 8.5 | 5 | 25.87 | 33.11 |
| 100 | 8.5 | 10 | 26.35 | 25.1 |
| 100 | 9.5 | 10 | 23.81 | 36.67 |
| 100 | 9.5 | 15 | 31.59 | 6.02 |
| 100 | 9.5 | 15 | 26.94 | 30.67 |

TABLE 7

1% 2-Methoxyethanol and Borate Buffer

| Molarity (mM) of citrate glycine buffer | pH | Incubator Time (mins) | Threshold Cycle | Abs. Fluor. |
|---|---|---|---|---|
| 10 | 9.5 | 5 | 24.78 | 25.74 |
| 10 | 9.5 | 15 | 26.25 | 27.98 |
| 10 | 9.5 | 15 | 26.79 | 27.83 |
| 10 | 11.25 | 5 | | 0.12 |
| 10 | 13 | 10 | 3.84 | 2.43 |
| 55 | 9.5 | 5 | 28.93 | 14.88 |
| 55 | 9.5 | 10 | 26.47 | 26.09 |
| 55 | 11.25 | 15 | 25.69 | 34.55 |
| 55 | 13 | 5 | | 0.94 |
| 55 | 13 | 5 | 35.64 | 1.51 |
| 55 | 13 | 15 | 5.55 | 7.09 |
| 100 | 9.5 | 5 | 28.11 | 18.73 |
| 100 | 9.5 | 5 | 28.95 | 9.64 |
| 100 | 9.5 | 15 | | 0.2 |
| 100 | 9.5 | 15 | | 0.22 |
| 100 | 11.25 | 5 | 26.21 | 14.28 |
| 100 | 11.25 | 10 | 25.08 | 35.51 |
| 100 | 13 | 10 | | 0.19 |
| 100 | 13 | 15 | | 0.13 |
| 100 | 13 | 15 | 13.26 | 1.01 |

The results again indicate that, in general, extraction solutions having an alkaline pH have better performance characteristics. With respect to the extraction solution containing a borate buffer, the extraction solutions having alkaline pH's less than 13 had optimal performance characteristics.

EXAMPLE 6

Detection of Extracted Nucleic Acid Via Ligase Chain Reaction

The effectiveness of the extraction solution according to the invention was tested through another detection method; the Ligase Chain Reaction (LCR). *Chlamydia trachomatis* elementary bodies obtained from infected McCoy cultured cells were added to PRESERVCYT® solutions (positive control). A specimen of PRESERVCYT® solution without the added elementary bodies provided the negative control. The samples then were extracted and subjected to LCR using the LCx Probe System of Abbott Laboratories (Abbott Park, Ill.) to test for CT DNA.

An elementary body-containing sample was divided into two aliquots. A first aliquot was extracted using Abbott's LCx reagents and Abbott's protocol for the processing urine specimens (i.e., LCx Urine Specimen Preparation Kit). The second aliquot was extracted through the process described in Example 1 using 100 μL of an extraction solution comprising 1% MCS in 2 mM borate buffer, pH 7.6, and 50 mM $MgCl_2$ (Solution 5). The DNA from both aliquots then was subjected to the remainder of the LCx assay (amplification and detection), which followed Abbott's standard procedure.

The manufacturer's recommendation for the determination of whether a sample was positive for CT DNA was followed in these experiments. More specifically, if the mean signal to cut off ratio (S/CO) was at least 1.00, the result was considered positive for CT DNA; if the S/CO was below 0.80, the result was considered negative; and any S/CO value in between was considered equivocal. The results are summarized in Table 9.

TABLE 9

| Specimen Type | Extraction Method | S/CO |
|---|---|---|
| Positive Control | With LCx reagents | 3.46 |
| Negative Control | With LCx reagents | 0.04 |
| Positive Control | With Solution 5 | 3.38 |
| Negative Control | With Solution 5 | 0.04 |

As shown in Table 9, the results obtained using Solution 5 were consistent with those using the extraction system included in the Abbott LCx system. Furthermore, the results also indicate that Solution 5 was compatible with the amplification reagents included in the Abbott LCx system.

EXAMPLE 8

Detection of *Neisseria gonorrhoeae*

An extraction solution according to the invention was tested for its ability to extract nucleic acid of a second organism, *Neisseria gonorrhoeae* (GC) from a biological sample. A variety of amplification-based detection methods were used to verify the presence of the extracted nucleic acid.

Approximately 100 µL of normal vaginal swab sample (collected in 2× Sucrose Phosphate Transport Buffer, available from Quelab Laboratories, Inc., Montreal, Quebec, Canada) was added to 21 vials each containing 1 mL of PRESERVCYT® solution. GC cells, previously collected from patients that exhibited genitourinary track infection, pelvic inflammatory disease, and disseminated gonococcal diseases then were added to each of the 21 sample vials. The GC cells added to the 21 vials were also shown via independent methodologies to be of 21 different GC strains. Two vials, each containing only 1 mL of PRESERVCYT® solution (i.e., without any cells) were used as negative controls. Another vial, containing GC DNA extracted via an independent method, provided a positive control.

The 24 sample vials were extracted as described in Example 1 using 1% MCS in 2 mM borate buffer, pH 9.5 (Solution 1). The resulting DNA samples were divided into two aliquots: one was subjected to conventional PCR and gel electrophoresis for DNA detection; the other aliquot was subjected to PCR with real time detection using a molecular beacon probe.

Conventional PCR for amplifying the first aliquot of GC DNA was performed with the HO1/HO3 primer set described in Ho et al., (1992) *Pathol.* 45:493–442. The HO1 primer contains the following sequence: 5'GCT-ACG-CAT-ACC-CGC-GTT-GC-3' (SEQ ID NO: 6). The HO3 primer's sequence is 5'CGA-AGA-CCT-TCG-AGC-AGA-CA-3' (SEQ ID NO: 7). This set of primers amplifies a 390 base pair DNA fragment of the cpp B gene in the GC DNA. Amplification was performed in 25 µL reaction volumes containing 10 mM Tris-HCl pH 8.3, 50 mM KCl, 2.5 mM MgCl$_2$, 200 µM of dNTP, 1 µM of each primer, and 1 unit of Platinum Taq polymerase (Perkin Elmer Cetus, P. E. Roche Molecular System, Inc., Branchburg, N.J., U.S.A) and 5 µL of DNA sample. The thermocycling step included an initial denaturation step at 94° C. for 4 minutes followed by 35 cycles each consisting of a 30 second denaturation step at 94° C., a one-minute annealing step at 60° C. and a 30 second extension step at 74° C. At the end of cycling, temperature was brought to 74° C., and kept at that temperature for 8 minutes.

Amplification products were fractioned via electrophoresis in a 2% agarose gel and were visualized with UV light after staining the gel with ethidium bromide. Twenty of the twenty one GC-containing specimens, generated a visible band of DNA of 390 base pairs, while neither negative control generated a product band. The results from conventional PCR detection method indicate that an MCS containing solution extracts nucleic acid sequence from GC.

The second aliquot of GC DNA specimens were PCR amplified with real time detection. The PCR amplification was conducted with the i-Cycler PCR System (Bio-Rad, Hercules, Calif.), using the following primer set: the forward primer 5'-GTCTTCGTTTCCAACAGGTCTA-3' (SEQ ID NO: 8) and the reverse primer 5'-TAGCGATATGGAGCGTCAAG-3' (SEQ ID NO: 9). Real time detection of amplified DNA products was performed by molecular beacon technology employing the following FAM and DABCYL labeled 42 mer molecular beacon probe: 5'TGGACGCTCTGTTTCGGCTCTCTGCT-GTTTCAAGTCCA 3' (SEQ ID NO: 10). Typically, real time PCR reaction was carried out in a 25 µL mixture containing 10 mM Tris-HCl pH 8.3, 50 mM KCl, 5 mM MgCl$_2$, 200 µM of dNTP, 1 µM of each primer, 1 Unit of Platinum Taq polymerase (Perkin Elmer Cetus), 50 nM molecular beacon, and 5 uL of target DNA. Typical thermocycling conditions included an initial denaturation step at 95° C. for 3 minutes followed by 60 cycles each consisting of a denaturation step at 95° C. for 30 seconds, primer and molecular beacon annealing steps at 55° C. for 45 seconds, and an extension step at 72° C. for 30 seconds.

After 60 thermocycles, samples that yielded less increase in their fluorescence reading than the negative control (PRESERVCYT® solutions containing no GC DNA) were considered negative and visa versa. All 21 GC-containing specimens (100%) yielded a positive reading.

In summary, different amplification-based detection steps show that MCS-containing solution successfully extracted a GC nucleic acid sequence with high selectivity.

EXAMPLE 9

Detection of Human Papillomavirus

An extraction solution according to the invention was tested for its ability to extract nucleic acid of Human papillomavirus (HPV) from a cell-containing sample.

Several cervical cell specimens stored in the PRESERV-CYT® solution were used as samples. These samples had previously been tested and genotyped, via independent methods, as containing cells that were infected with high risk HPV strains. The specimens were divided into equal aliquots. The first aliquot was extracted using the commercially available QIAamp® DNA Mini Kit (Qiagen, Valencia, Calif.). Extraction by the Qiagen QIAamp® DNA Mini Kit was performed on cells harvested from the samples by centrifugation in accordance with the manufacturer's instructions for processing blood and body fluid spin samples. The second aliquot was extracted using the process described in Example 1 with 1% MCS in 2 mM borate buffer, pH 9.5 (Solution 1).

The resulting samples were then analyzed by conventional PCR. A cocktail of forward and reverse primers that amplify part of the E6 regions of several high-risk HPV strains were used. A typical DNA master mix was prepared in a final volume of 25 µL containing 10 mM Tris-HCl pH 8.3, 50 mM KCl, 1.5 mM $MgCl_2$, 200 µM of dNTP, 0.5 µM of each primer cocktail (forward and reverse), 1.25 Units of Platinum Taq polymerase (Perkin Elmer Cetus, P.E. Roche Molecular System, Inc., Branchburg, N.J., U.S.A), and 3 µL of target DNA.

PCR was performed under the following thermocycling conditions: initial denaturation at 94° C. for 5 minutes followed by 40 cycles of 94° C. for 1 minute, 48° C. anneal for 1 minute, and 72° C. extension for 1 minute. A final extension at 72° C. for 8 minutes was performed following the PCR cycling process. Following PCR, the amplification products were fractionated by electrophoresis through a 2.5% agarose gel and visualized with UV light after staining with ethidium bromide.

The results indicated that HPV nucleic acids could be extracted using both Solution 1 and the QIAamp® DNA Mini Kit, and that the resulting nucleic acids could be amplified by PCR. The product bands were consistent with the expected lengths for various HPV strains including types 45 and 31. No DNA amplicon was observed in PRESERV-CYT® samples that had tested negative for HPV DNA. These results suggest that MCS-containing solution can be useful for the extraction and subsequent analysis of extracted HPV nucleic acid.

The content of each patent and non-patent document identified herein is expressly incorporated by reference herein.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Other embodiments of the invention are within the following claims.

What is claimed is:

1. A method of extracting nucleic acid from a biological sample, the method comprising: mixing the sample with a solution comprising about 1% 2-methoxyethanol and borate buffer, so that nucleic acid is released from cells or cellular debris in the sample.

2. The method of claim 1, wherein the solution has a pH greater than about 7.

3. The method of claim 2, wherein the pH is greater than about 7 and less than about 13.

4. The method of claim 1 comprising the additional step of heating the mixture to a temperature within the range of from about 50° C. to about 100° C.

5. The method of claim 4, comprising heating the mixture to a temperature of from about 75° C. to about 100° C.

6. The method claim 5, comprising heating the mixture to a temperature of from about 90° C. to about 100° C.

7. The method of claim 1, comprising the additional step of amplifying a nucleic acid sequence extracted from the sample.

8. The method of claim 1, comprising the additional step of detecting a nucleic acid sequence extracted from the sample.

9. The method of claim 7, wherein the amplification step uses a pair of amplification primers comprising the sequences of SEQ ID NOS: 4 and 5.

10. The method of claim 9, comprising the additional step of detecting the presence of the nucleic acid sequence with a probe comprising the sequence of SEQ ID NO: 3.

11. The method of claim 7, wherein the amplification step uses a pair of amplification primers comprising the sequences of SEQ ID NOS: 8 and 9.

12. The method of claim 11, comprising the additional step of detecting the presence of nucleic acid sequence a probe comprising the sequence of SEQ ID NO: 10.

13. The method of claim 1, wherein the method lacks a chloroform extraction step, a phenol extraction step, a phenol/chloroform extraction step, or an alcohol precipitation step.

14. The method of claim 1, wherein the nucleic acid is a bacterial or viral nucleic acid.

15. The method of claim 1, wherein the biological sample is harvested from a mammal.

16. The method of claim 15, wherein the biological sample comprises cervical cells or cell debris.

17. The method of claim 15, wherein the biological sample comprises breast cells or cell debris.

* * * * *